US012679862B2

(12) United States Patent
Liu et al.

(10) Patent No.: US 12,679,862 B2
(45) Date of Patent: Jul. 14, 2026

(54) HEMP SEED PROTEIN PICKERING PARTICLES AND A METHOD FOR PREPARING HEMP SEED PICKERING EMULSION

(71) Applicant: Jiangnan University, Wuxi (CN)

(72) Inventors: Yuanfa Liu, Wuxi (CN); Xiuhang Chai, Wuxi (CN); Yanwen Sun, Wuxi (CN); Wanjun Han, Wuxi (CN)

(73) Assignee: Jiangnan University, Wuxi (CN)

( * ) Notice: Subject to any disclaimer, the term of this patent is extended or adjusted under 35 U.S.C. 154(b) by 322 days.

(21) Appl. No.: 18/244,157

(22) Filed: Sep. 8, 2023

(65) Prior Publication Data

US 2023/0416302 A1      Dec. 28, 2023

Related U.S. Application Data

(63) Continuation of application No. PCT/CN2022/138679, filed on Dec. 13, 2022.

(30) Foreign Application Priority Data

May 30, 2022    (CN) .......................... 202210596188.5

(51) Int. Cl.
C07K 1/14          (2006.01)
C07K 1/30          (2006.01)

(52) U.S. Cl.
CPC ................ C07K 1/145 (2013.01); C07K 1/30 (2013.01)

(58) Field of Classification Search
None
See application file for complete search history.

(56) References Cited

FOREIGN PATENT DOCUMENTS

| CN | 110917064 A | 3/2020 |
|---|---|---|
| CN | 112544991 A | 3/2021 |
| CN | 115152888 A | 10/2022 |

| CN | 117651494 A | * | 3/2024 | ................ A23J 3/14 |
|---|---|---|---|---|
| WO | 2014140023 A1 | | 9/2014 | |
| WO | WO-2023231364 A1 | * | 12/2023 | .............. A23J 1/006 |

OTHER PUBLICATIONS

Kostic et al. (Industrial Crops and Products, 2013, vol. 48, pp. 133-143).*
Zhang et al. (Cellulose, 2018, vol. 25, pp. 4107-4120) and Duffus et al. (University of Birmingham: J. of Colloid and Interface Science, vol. 473, 2016, pp. 9-21).*
Duffus et al. (University of Birmingham: J. of Colloid and Interface Science, vol. 473, 2016, pp. 9-21).*
Li et. al. "preparation and characterization of peanut protein nanoparticles" Food and Oils. Vol 28, Issue 05. May 1, 2015.
Yijun Pana et.al. "Structure, assembly and application of novel peanut oil body protein extracts nanaparticles" Food Chemistry, V 367, Jan. 15, 2022.
Xu et. al. "The extraction of Hemp seed protein and its physicochemical properties" Food research and development. V 42, Issue 3, Feb. 10, 2021.
"Bakery Basics: bread, Chinese bakery and western bakery goods", Jan. 31, 2005. p. 117-118.
Wu et. al. "Effects of hulling treatment on extraction, functinal properties and digestibility of hemp protein" Journal of Food Science and Technology. vol. 49, No. 4, Jul. 25, 2021.

* cited by examiner

*Primary Examiner* — Hope A Robinson
(74) *Attorney, Agent, or Firm* — IPro, PLLC; Na Xu

(57) ABSTRACT

Disclosed are hemp seed protein Pickering particles as well as a preparation method and application thereof, belonging to the field of multi-component restructured foods. The preparation of Pickering emulsion based on hemp seed protein Pickering nanoparticles includes: preparing hemp seed protein Pickering particles by using an anti-solvent precipitation method under the condition of taking hemp seed protein as a raw material, formic acid and water as solvents; then, adding the prepared hemp seed protein Pickering particles into water together with maltodextrin and corn syrup solids for fully dissolving to form a homogeneous suspension; and adding vegetable oil into the suspension and mixing well to obtain the Pickering emulsion. The Pickering emulsion is high in stability, and powdered oil constructed by using same has the advantages of being environmentally-friendly, cost-saving, and easy to achieve high stability and high unsaturation, thus having wide application value in food and medicine fields.

6 Claims, 10 Drawing Sheets

HEMP SEED PROTEIN PICKERING PARTICLES AND A METHOD FOR PREPARING HEMP SEED PICKERING EMULSION

TECHNICAL FIELD

The present disclosure discloses hemp seed protein Pickering particles as well as a preparation method and application thereof, belonging to the field of multi-component restructured foods.

BACKGROUND

Powdered oils are powder products made from vegetable oils, carbohydrates, proteins, emulsifiers, and other raw materials, which are embedded and processed by employing a microencapsulation technology. The powdered oils are widely used in infant formula milk powder, baking, beverages and other food fields. The use of high-saturation oils and low molecular weight surfactants (LWSFs) is a difficult problem restricting the development of powdered oil technologies. The former is closely related to the high incidence of cardiovascular and cerebrovascular diseases, while the latter is prone to bring potential safety problems. In the process of powdered oil processing, it is generally necessary to construct an oil-in-water (O/W) emulsion system, but the physical stability of the emulsion system prepared by the conventional emulsification method has not been ideal.

The construction of a Pickering emulsion system in a powdered oil processing technology is expected to enhance the physical stability and oxidative stability of powdered oil, thus achieving the improvement of powdered oil unsaturation.

Pickering emulsion is an emulsion system stabilized by solid particles irreversibly adsorbed onto an oil-water interface. The solid particles endow the Pickering emulsion with a variety of excellent properties, such as extensive sources, low toxicity, excellent physical stability, and outstanding antioxidant capacity. In the study of Anja Schröder et al., matcha and pineapple leaf granular powder were used to prepare Pickering emulsion, and it was found that they could effectively inhibit emulsion flocculation. In addition, the contents of their primary oxidation products and secondary oxidation products during storage were only a quarter of those in a control group.

Hemp, also known as China-hemp, is a renewable economic crop in China with a large output. Hemp seed protein is mainly composed of edestin, and the edestin has balanced amino acids, making it a complete protein. Due to the poorer water solubility, water binding capacity and emulsifying property of the hemp seed protein, its development and utilization remained in the primary stage for a long time. For example, Pengwei Xu et al. found that the solubility of the hemp seed protein was extremely low at a pH value of 7.0, only 1.57%, and the water binding capacity of the hemp seed protein was also positively related to its solubility.

At present, some scholars have modified the hemp seed protein to improve its application characteristics. However, these modification studies are complex in processes, introduce a variety of chemicals, and are low in environmental friendliness. The construction of Pickering emulsion from hemp seed protein is a new strategy for efficient and green utilization of the hemp seed protein.

SUMMARY

It is the first objective of the present disclosure to provide a method for preparing powdered oil based on hemp seed protein Pickering particles, so as to solve the technical problems of using more saturated oil, safety hazards caused by low molecular weight surfactants, and poorer physical stability caused by the conventional emulsification methods in the powdered oil production process.

It is a further objective of the present disclosure to achieve high-value utilization of hemp seed protein, so as to solve the technical problems of difficulty in utilization and plenty of waste caused by poorer self-emulsification, water solubility and water absorption of the hemp seed protein.

In order to solve the above-mentioned technical problems, the present disclosure provides a method for stabilizing Pickering emulsion based on the hemp seed protein Pickering particles, and then constructing highly unsaturated powdered oil. The technical solution adopted in the present disclosure includes: extracting hemp seed protein by means of alkali-soluble acid precipitation, preparing hemp seed protein Pickering nanoparticles by using an anti-solvent precipitation method under the condition of taking the hemp seed protein as a raw material, formic acid and water as solvents, controlling nanoparticle sizes and three-phase contact angles by adjusting reaction conditions to further construct highly stable Pickering emulsion, and finally spray-drying to obtain the powdered oil. The method is economical, simple and convenient, safe, and green.

The technical solution of the present disclosure is described below.

The first objective of the present disclosure is to provide a method for preparing hemp seed protein Pickering nanoparticles, which includes the following steps:

(1) crushing hemp seeds to obtain crushed hemp seeds, removing oil from the hemp seeds by means of n-hexane solvent extraction, and then performing alkali-soluble acid precipitation treatment on the residue to obtain hemp seed protein powder;

(2) dissolving the hemp seed protein powder in a formic acid solution to prepare a hemp seed protein stock solution, and then adding the hemp seed protein stock solution dropwise into deionized water under stirring conditions; and (3) centrifuging a suspension obtained in step (2) to remove the bottom precipitate and then adjusting the pH value, precipitating hemp seed protein nanoparticles, then carrying out suction filtration to obtain protein particle precipitate, and freeze-drying the protein particle precipitate to obtain dried Pickering particles.

As an embodiment of the present disclosure, the hemp seeds used may be, but not limited to those produced in the Bama region of Guangxi.

As an embodiment of the present disclosure, the ratio of n-hexane to the crushed hemp seeds used in step (1) is (5:1)-(10:1) (w/w).

As an embodiment of the present disclosure, the alkali-soluble acid precipitation in step (1) is performed under the conditions that the alkali dissolution pH value is 8.0-11.0, and the acid precipitation pH value is 3.0-5.5.

As an embodiment of the present disclosure, the ratio of the formic acid solution to the hemp seed protein powder used in step (2) is (10:1)-(20:1) (w/w).

As an embodiment of the present disclosure, the mass fraction of formic acid in the formic acid solution in step (2) is 88%, and the rest is water.

As an embodiment of the present disclosure, in step (2), the stirring mode is mechanical stirring or magnetic stirring, and a stirring speed is 5000-10000 rpm.

As an embodiment of the present disclosure, the method for adding the hemp seed protein stock solution dropwise in step (2) includes using a dropping funnel to add drop by drop, and a dropwise addition speed is 4-20 ml/min.

As an embodiment of the present disclosure, the ratio of the protein stock solution to the deionized water used in step (2) is (1:10)-(1:20) (v/v).

As an embodiment of the present disclosure, the pH condition of the precipitation in step (3) is 3.0-5.5.

The present disclosure also utilizes the hemp seed protein Pickering particles prepared by the above method.

The second objective of the present disclosure is application of the Pickering particles prepared as described above in nutritional food, baked food and beverages.

As an embodiment of the present disclosure, the application is to construct a Pickering emulsion system based on the aforementioned Pickering nanoparticles, which specifically includes the following steps: adding the hemp seed protein Pickering particles into water together with maltodextrin and corn syrup solids for fully dissolving to form a homogeneous suspension; and adding vegetable oil into the prepared suspension and mixing well to obtain Pickering emulsion.

As an embodiment of the present disclosure, the solid contents are as follows: the hemp seed protein Pickering particles account for 0.5%-3% (w/w), maltodextrin accounts for 13.5%-36% (w/w), and corn syrup accounts for 13.5%-36% (w/w).

As a specific embodiment of the present disclosure, the dissolving method includes: first, initially stirring with a glass rod or in a manner of mechanical stirring, then magnetically stirring for 30 min at 75° C. under the condition of a rotating speed being 700 rpm, and stirring at room temperature for 12 h after stopping heating.

As a specific embodiment of the present disclosure, the vegetable oil may be flaxseed oil, microalgae oil, peony seed oil, perilla seed oil, and the like, but not limited to the above oils.

As an embodiment of the present disclosure, the homogeneous suspension is formed by adding the hemp seed protein Pickering particles into water together with the maltodextrin and corn syrup solids for fully dissolving, and then stirring, shearing at a high speed and homogenizing.

As an embodiment of the present disclosure, the stirring condition is magnetic stirring or mechanical stirring, with a stirring speed of 700-1000 rpm and a stirring time of 30-60 min.

As an embodiment of the present disclosure, the high-speed shearing is performed at 8000-12000 rpm for 3 min, and the high-speed shearing occurs every 30 s for 30 s.

As an embodiment of the present disclosure, the homogenization condition is that an ultrasonic cell disruptor is used at a power of 100-800 W for 10 min, and the ultrasonic homogenization is performed every 5 s for 5 s.

The Present Disclosure has the Following Beneficial Effects.

(1) The Pickering particles prepared from the hemp seed protein have a particle size range of 200-400 nm and have stronger adsorption energy so as to be irreversibly adsorbed onto an oil-water interface, which greatly improves the stability of the emulsion during powdered oil processing, and overcomes the problem of poorer physical stability caused by the conventional emulsification methods.

(2) The hemp seed protein is rich in nutrients and has a coordinated amino acid ratio. It is a complete protein and has the characteristics of low toxicity. Replacing low molecular weight surfactants with the hemp seed protein particles can avoid potential safety hazards during the use of the low molecular weight surfactants, and thus improves the consumption experience of powdered oils.

(3) The anti-solvent precipitation method only uses two common solvents in the process of preparing the Pickering particles, which is efficient, green, safe and economical.

(4) In addition, the present disclosure proposes a new idea for efficient utilization of the hemp seed protein. By constructing the Pickering emulsion, the problems of poor protein emulsification, poor water absorption and poor water solubility in the conventional utilization scene of the hemp seed protein are effectively avoided, thus breaking the bottleneck that the hemp seed protein is difficult to use properly for a long time.

DETAILED DESCRIPTION

The main idea of the present disclosure is to provide a new solution to solve the potential safety hazards (the use of saturated oils and low molecular weight surfactants) and poorer physical stability in the conventional powdered oil preparation process, that is, to replace the conventional low molecular weight surfactants with hemp seed protein Pickering nanoparticles processed from hemp seed protein for stabilizing powdered oils.

According to the present disclosure, the Pickering particles are firstly prepared, the conditions for the formation process of Pickering emulsion are optimized, and highly unsaturated powdered oil is finally constructed. The process includes: separation of hemp seed protein, preparation of Pickering particles, Pickering emulsion construction, optimization of conditions, as well as processing and producing of various highly unsaturated powdered oils.

The present disclosure will be described in further detail below with reference to specific examples, but the scope of protection claimed in the present disclosure is not limited to the scope described in the examples.

The Bama hemp seeds in the following examples are produced in the Bama region of Guangxi.

Example 1 Preparation of Hemp Seed Protein Pickering Nanoparticles (1) 500 g of Bama hemp seeds were mechanically crushed, and 2500 g of n-hexane (analytical grade) was added to the crushed hemp seeds, stirred at a stirring speed of 700 rpm for 3 h, and then allowed to stand for stratification. After liquid stratification occurred, the n-hexane in a beaker was poured out, and the solid part was placed in a ventilated place for ventilation overnight so as to remove the residual n-hexane; and the above steps were repeated once.

(2) 2500 mL of deionized water was added to the solids obtained in step (1), with a pH value being adjusted to 9.5. The mixture was stirred at 700 rpm for 5 h and then centrifuged by a centrifuge for 10 min under a centrifugal force of 24000 g, and the centrifugal precipitate was discarded. After that, the pH value of the solution subjected to centrifugation was adjusted to After the protein was fully precipitated, the centrifuge was used to perform centrifugation for 10 min under the centrifugal force of 24000 g to obtain the solid precipitate of hemp seed protein. The precipitate of the hemp seed protein was freeze-dried, so that hemp seed protein powder (411.15 g, with an extraction rate of 82.23%) was obtained.

Figure 3A:
FIG. 3A is magnification 500 SEM images of hemp seed protein Pickering nanoparticles.
Figure 3B:
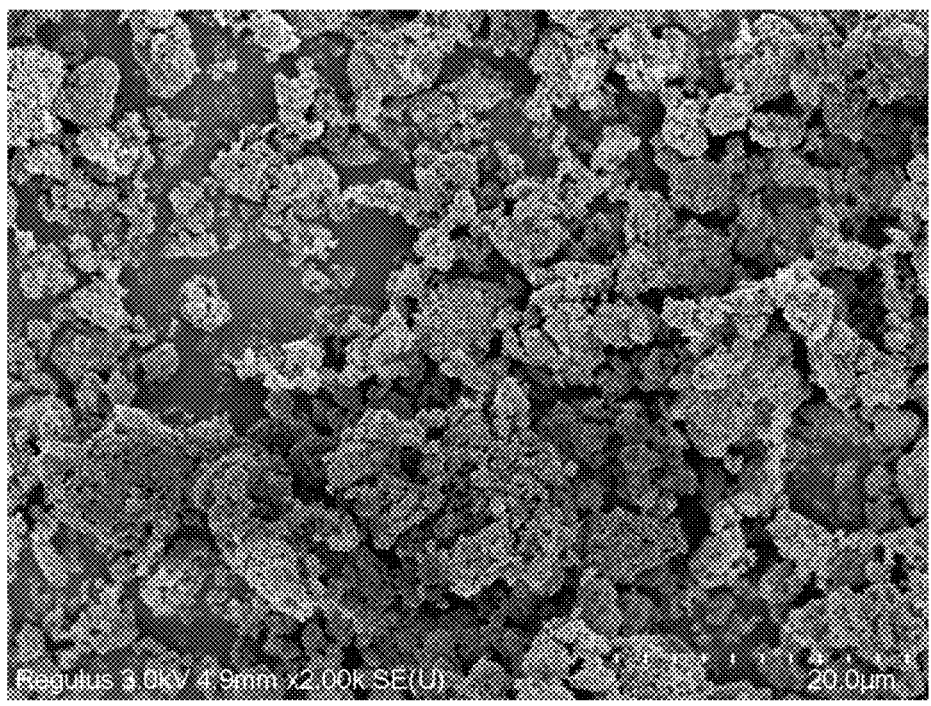
FIG. 3B is magnification 2K SEM images of hemp seed protein Pickering nanoparticles.
Figure 3C:
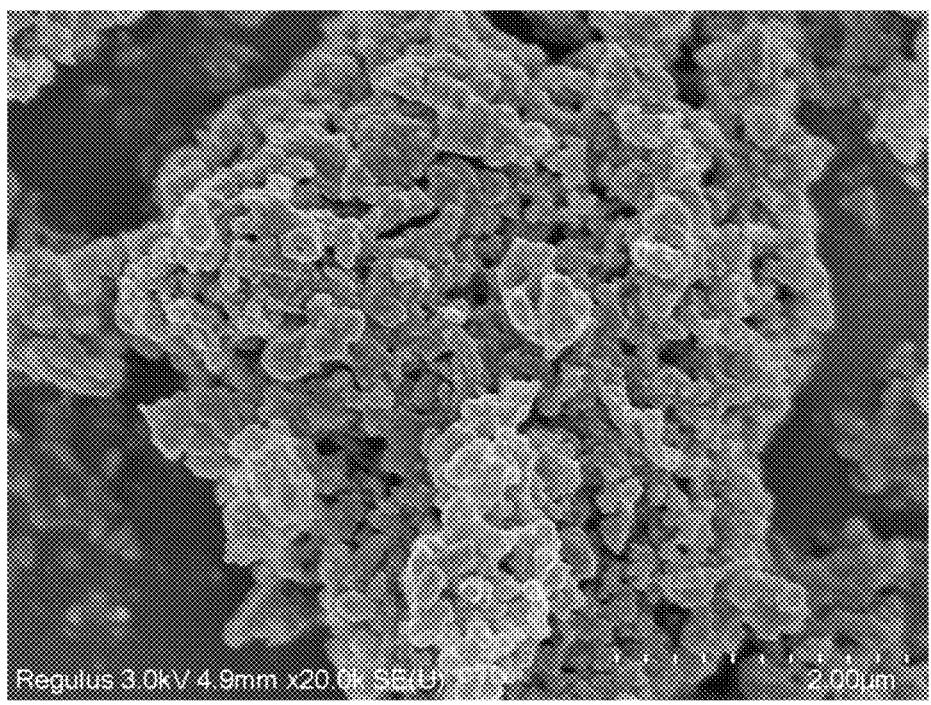
FIG. 3C is magnification 20K SEM images of hemp seed protein Pickering nanoparticles.
Figure 3D:
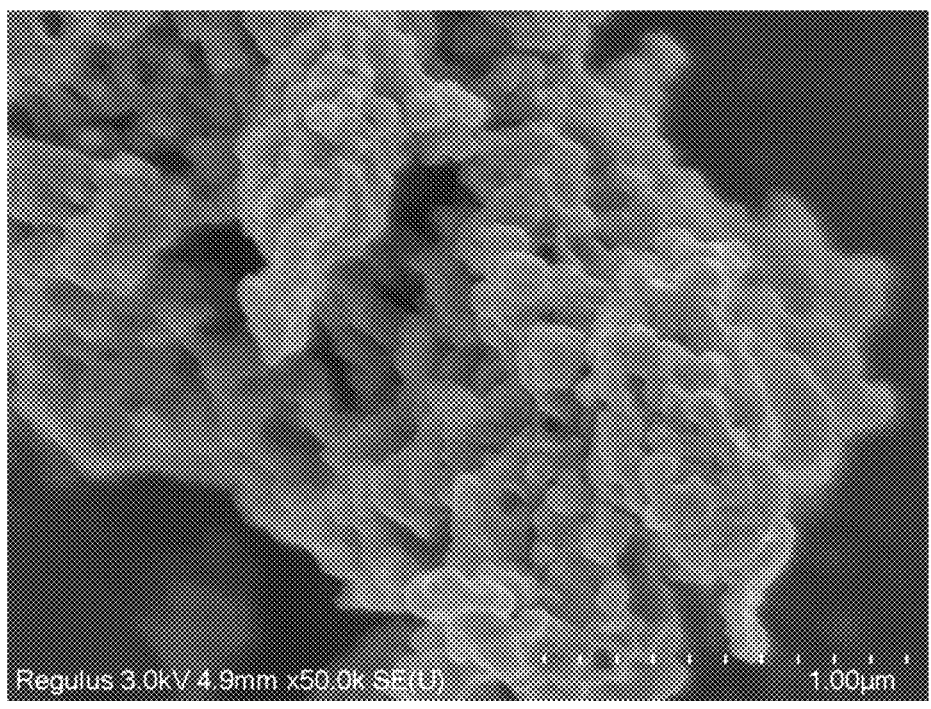
FIG. 3D is magnification 50K SEM images of hemp seed protein Pickering nanoparticles.

(3) 200 g of the hemp seed protein powder obtained in step (2) was fully dissolved in 2500 g of a formic acid solution (88%, analytical grade) to form a hemp seed protein stock solution. Then, the stock solution was added dropwise to 15 L of deionized water, the deionized water was mechanically stirred during the dropwise addition, a dropwise addition speed was 4 mL/min, and a stirring speed was maintained at 1000 rpm. After that, the deionized aqueous solution of the hemp seed protein was centrifuged for 10 min under a centrifugal force of 10000 g to remove the precipitate. A NaOH aqueous solution with a pH value of 9.5 was used to adjust the pH value to about 4.5 until flocculent precipitate appeared in the solution, and the precipitate was separated by means of suction filtration, so that hemp seed protein Pickering nanoparticles were obtained. The morphology of the hemp seed protein Pickering nanoparticles is shown in FIG. 3A"FIG. 3D.

Figure 1A:
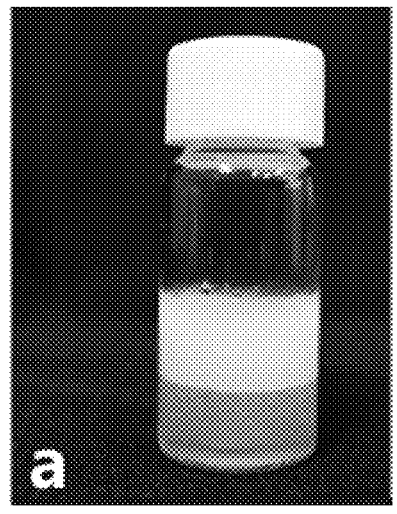
FIG. 1A is an apparent diagram of Pickering emulsion with 0.1% addition of hemp seed protein nanoparticles.
Figure 1B:
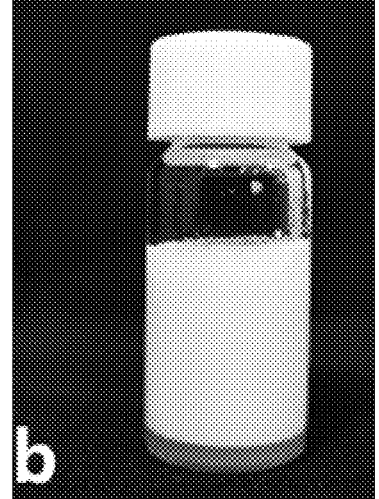
FIG. 1B is an apparent diagram of Pickering emulsion with 0.5% addition of hemp seed protein nanoparticles.
Figure 1C:
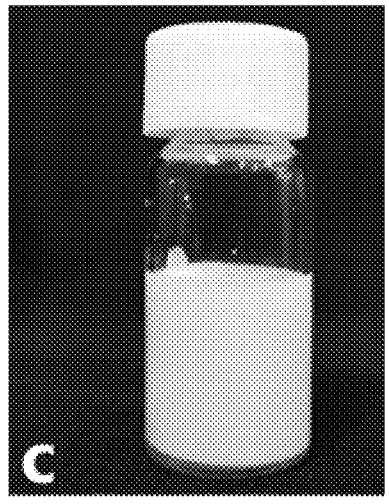
FIG. 1C is an apparent diagram of Pickering emulsion with 1% addition of hemp seed protein nanoparticles.
Figure 1D:
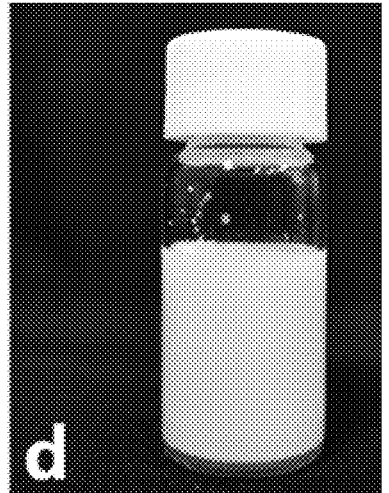
FIG. 1D is an apparent diagram of Pickering emulsion with 2% addition of hemp seed protein nanoparticles.
Figure 1E:
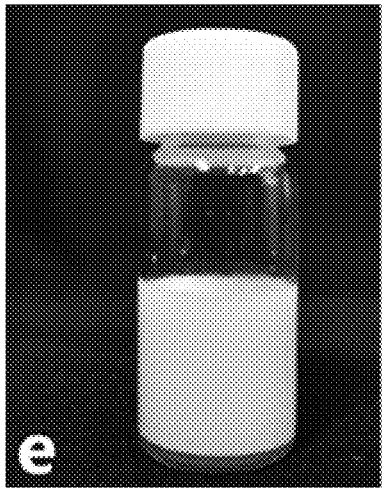
FIG. 1E is an apparent diagram of Pickering emulsion with 3% addition of hemp seed protein nanoparticles.
Figure 2:
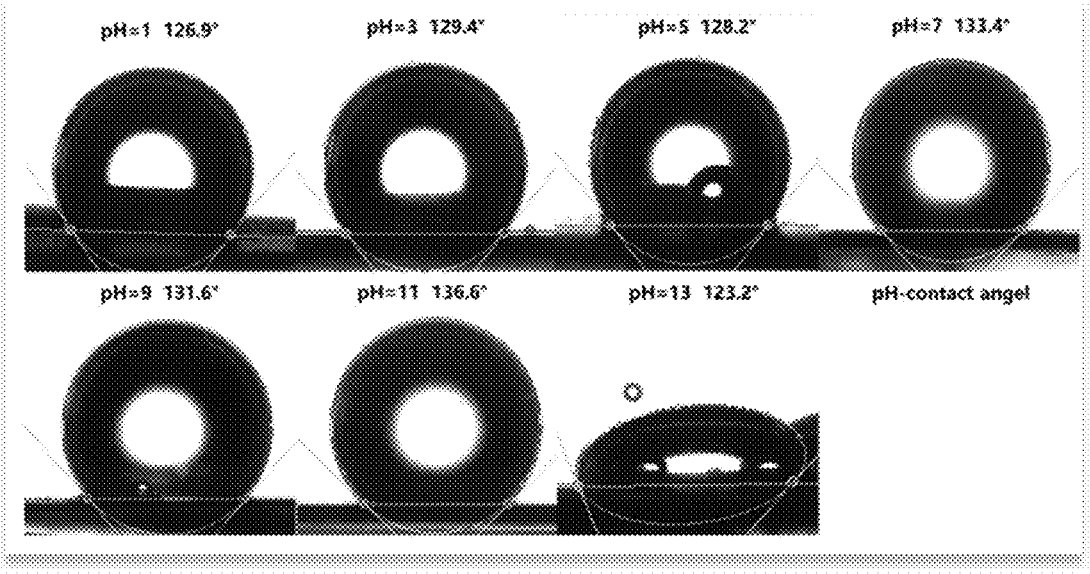
FIG. 2 shows effects of different pH values on three-phase contact angles of hemp seed protein Pickering particles.
Figure 2:
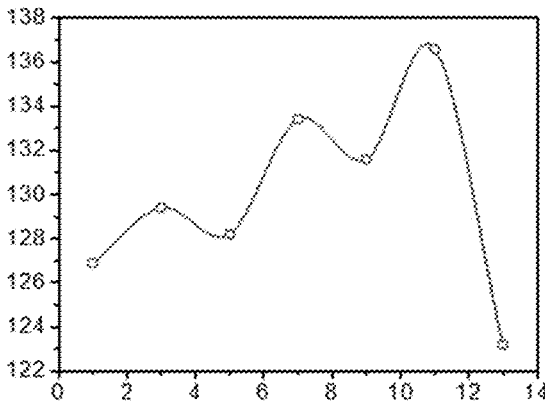

Example 2 Effect of pH Values on Hemp Seed Protein Pickering Particles 0.5 g of hemp seed protein Pickering particles prepared in Example 1 were pressed into a sheet with a thickness of 1 mm by a sheet press, and then three-phase contact angles of the hemp seed protein Pickering particles were respectively measured when the pH value is 1, 3, 5, 7, 9, 11, or 13. The results are shown in Table 1 and FIG. 2.

TABLE 1

| The effect of pH values on three-phase contact angles of hemp seed protein Pickering particles | | | | | | | |
|---|---|---|---|---|---|---|---|
| pH value | 1 | 3 | 5 | 7 | 9 | 11 | 13 |
| Three-phase contact angle (°) | 126.9 | 129.4 | 128.2 | 133.4 | 131.6 | 136.6 | 123.2 |

From the results, it can be seen that as the pH value increases, the three-phase contact angles of the hemp seed protein Pickering particles show a trend of first increasing and then decreasing. The three-phase contact angle value needs to be within a range of 30°-150° if the Pickering particles are expected to be stable, so that the prepared Pickering particles shall meet the requirement for the contact angle. On the other hand, the effect of the pH values on the three-phase contact angles is largely related to a protein isoelectric point, around which the Pickering particles exhibit stronger hydrophobicity.

Example 3: Effect of Formic Acid Aqueous Solution Concentration on Hemp Seed Protein Pickering Particles (1) Same as step (1) of Example 1;

(2) same as step (2) of Example 1; and (3) 50 g of hemp seed protein powder was taken and dissolved in each of 625 g of formic acid aqueous solutions with different concentrations (0%, 10%, 20%, 30%, 40%, 50%, 60%, 70%, 88%, and 98%) to form hemp seed protein stock solutions respectively. Stock supernatant was added dropwise to 3.75 L of deionized water at a rate of 4 ml/min. The deionized water was mechanically stirred during the dropwise addition and the stirring speed was maintained at 1000 rpm. The obtained particle suspension was then diluted 10 times, and the particle sizes and $\zeta$-potential were measured by using a Zetasizer nano ZS particle sizer from Malvern Company, UK. The results are shown in Table 2 below.

TABLE 2

| Effect of formic acid aqueous solution concentrations on particle sizes of hemp seed protein Pickering particles and $\zeta$-potential | | | |
|---|---|---|---|
| Serial number | Formic acid aqueous solution concentration (%, v/v) | Particle size (nm) | $\zeta$-potential (mV) |
| 1 | 0 | —* | — |
| 2 | 10 | — | — |
| 3 | 20 | 2366.23 ± 12.0 | 11.33 ± 0.707 |
| 4 | 30 | 1356.44 ± 24.5 | 21.55 ± 2.001 |
| 5 | 40 | 973.76 ± 8.6 | 22.35 ± 2.305 |
| 6 | 50 | 473.60 ± 4.2 | 27.50 ± 3.233 |
| 7 | 60 | 376.66 ± 10.3 | 32.37 ± 2.106 |
| 8 | 70 | 531.50 ± 2.8 | 33.56 ± 1.640 |
| 9 | 88 | 543.47 ± 7.0 | 36.72 ± 2.909 |
| 10 | 98 | 568.55 ± 8.9 | 35.43 ± 2.772 |

—*The particle sizes of the hemp seed protein Pickering particles in 0% and 10% formic acid aqueous solutions exceeded the maximum detection range.

It can be seen from the data in the table that with the increase of the concentration of the formic acid aqueous solution for dissolving hemp seed protein, the particle sizes of the Pickering particles finally formed tends to decrease, but after the concentration of 60%, the particle sizes basically remain around 550 nm. In addition, the ζ-potential has an upward trend. From the previous research results, when the ζ-potential is greater than ±30, the formed emulsion is relatively stable.

Example 4 Preparation of Pickering Emulsion Stabilized by Hemp Seed Protein Pickering Particles 0.02 g, 0.1 g, 0.2 g, 0.4 g, and 0.6 g of the hemp seed protein Pickering particles prepared in Example 1 were fully dissolved in 14 g of deionized water respectively together with 2.7 g of maltodextrin and 2.7 g of corn syrup to prepare a hemp seed protein Pickering particle suspension. The dissolution conditions were as follows: initial stirring was firstly performed by using a glass rod or in a manner of mechanical stirring, magnetic stirring was then carried out for 30 min at 75° C. under the condition of a rotating speed being 700 rpm, and the product was stirred at room temperature for 12 h after stopping heating.

Then, 20 g of flaxseed oil was added to each of the hemp seed protein Pickering particle suspensions, and the mixture was stirred uniformly in a manner of magnetic stirring or mechanical stirring, with a stirring speed being 800 rpm and a stirring time being 40 min. After that, high-speed shearing was performed on the above liquid at 10000 rpm for 3 min, and the high-speed shearing occurred every 30 s for 30 s. The obtained Pickering emulsion was stored at room temperature for 24 h, and its apparent diagram is shown in FIG. 1A~FIG. 1E.

Figure 4A:
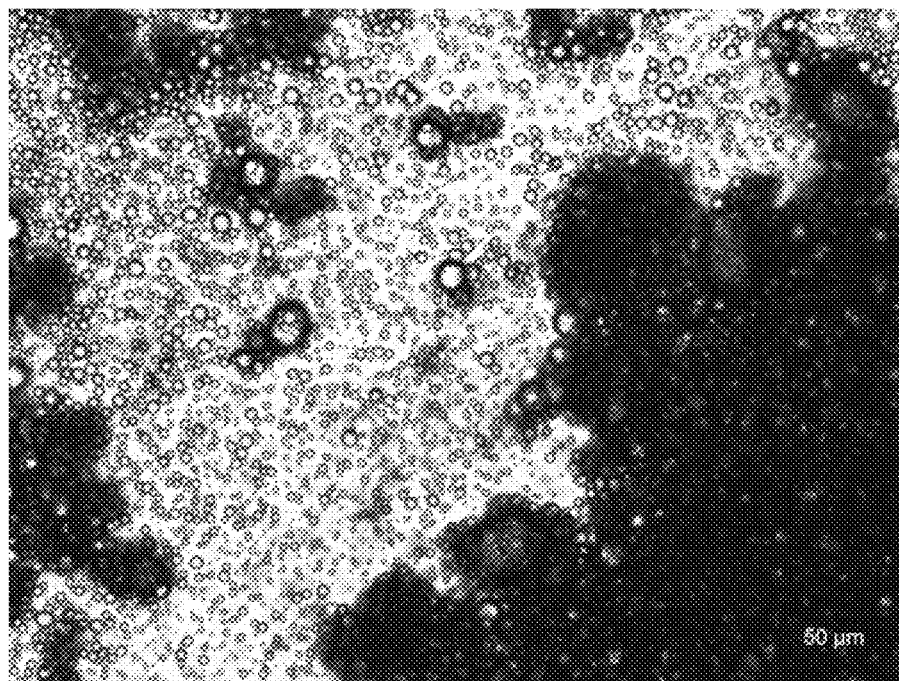
FIG. 4A shows a magnification 20×10 microstructure of Pickering emulsion stabilized by 3% hemp seed protein nanoparticles.
Figure 4B:
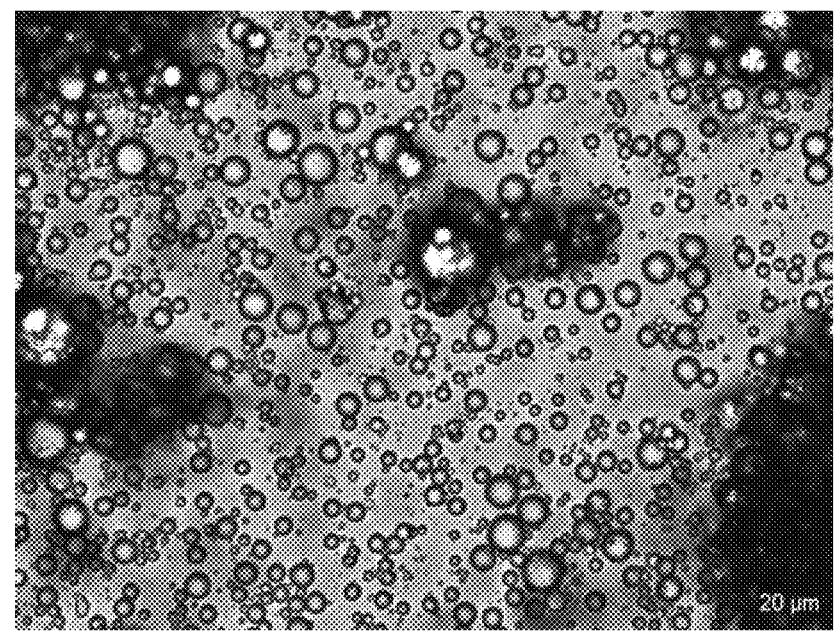
FIG. 4B shows a magnification 50×10 microstructure of Pickering emulsion stabilized by 3% hemp seed protein nanoparticles.
Figure 4C:
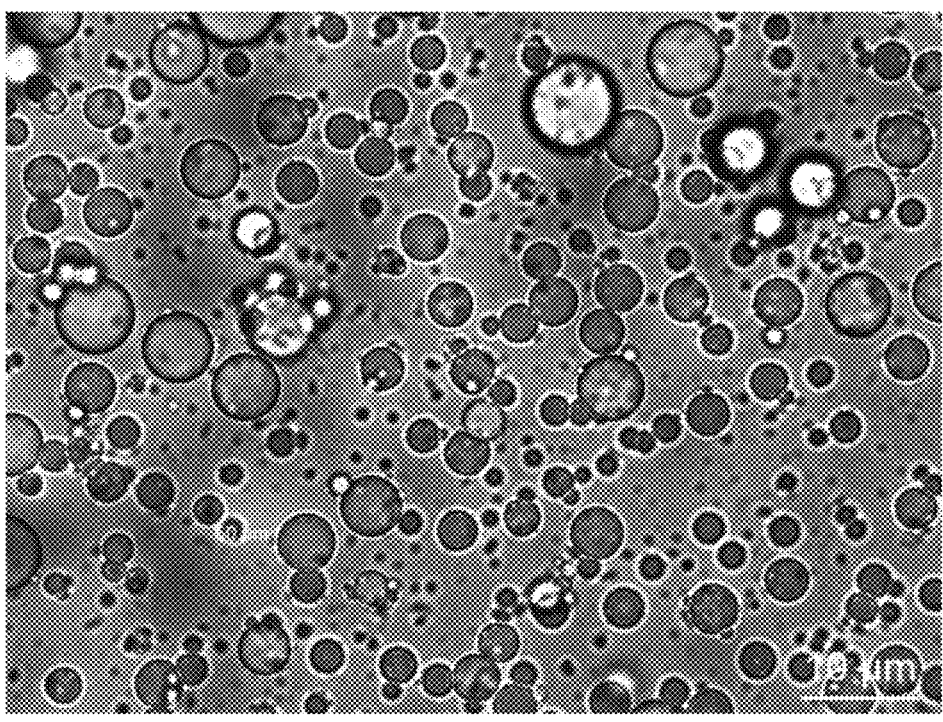
FIG. 4C shows a magnification 100×10 microstructure of Pickering emulsion stabilized by 3% hemp seed protein nanoparticles.

The microstructure of the emulsion with 3% of hemp seed protein Pickering particles added was observed via an optical microscope. The results are shown in FIG. 4A~FIG. 4C. The results in the figure show that the particle size of the Pickering emulsion containing 3% hemp seed protein is 10 μm or less after storage for 24 h.

Figure 5:
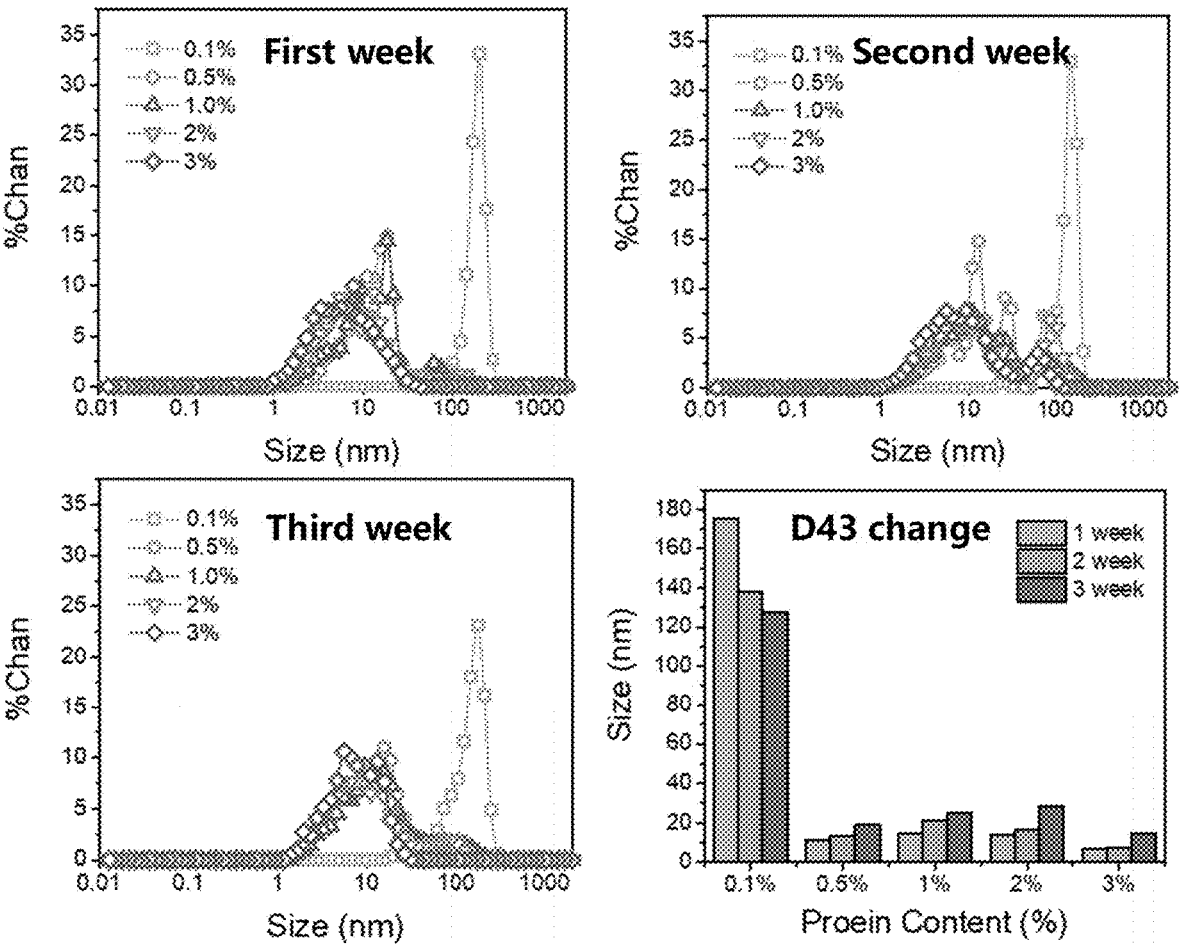
FIG. 5 shows effect of the addition amount (0.1%, 0.5%, 1%, 2%, or 3% (w/w)) of hemp seed protein Pickering particles on the storage stability (particle size) of Pickering emulsion.
Figure 6:
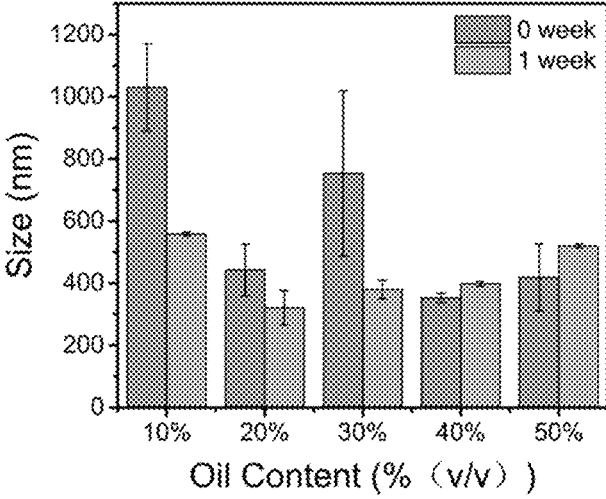
FIG. 6 shows effects of different oil-water ratios (1:9, 2:8, 3:7, 4:6, and 5:5) on the storage stability (particle size) of Pickering emulsion.

Example 5 Effect of Addition Amount of Hemp Seed Protein Pickering Particles on Emulsion The preparation method in Example 4 was used to prepare Pickering emulsions with 0.1%, 0.5%, 1%, 2% and 3% of hemp seed protein Pickering particles added, and then all the emulsions were stored at 20° C. to determine their storage stability. After that, particle size analysis was performed by using a laser particle size analyzer S3500 from Microtrac Company, USA, respectively under the conditions that the storage time is 7 days, 14 days and 21 days. The results are shown in FIG. 5.

From the results in the figure, it can be found that the Pickering emulsion with 0.1% of the hemp seed protein Pickering particles added has extremely poor stability, which is basically not stable emulsion. At all addition amounts other than this, the Pickering emulsions are efficiently formed and stable. With the increase of the hemp seed protein Pickering particle concentration, the particle size of the Pickering emulsion shows a decreasing trend. On the other hand, the storage time has a great influence on emulsion stability, and the particle sizes of the Pickering emulsions at all concentrations increase with the prolongation of the storage time. The results show that the Pickering emulsion system constructed when the addition amount of the hemp seed protein Pickering particles is 3% has better stability.

Example 6 Preparation of Highly Unsaturated Powdered Oil with Flaxseed Oil as Core Material 0.6 g of the hemp seed protein Pickering particles prepared in Example 1 were fully dissolved in 14 g of deionized water together with 2.7 g of maltodextrin and 2.7 g of corn syrup to prepare a hemp seed protein Pickering particle suspension. The dissolution conditions were as follows: initial stirring was firstly performed by using a glass rod or in a manner of mechanical stirring, magnetic stirring was then carried out for 30 min at 75° C. under the condition of a rotating speed being 700 rpm, and the product was stirred at room temperature for 12 h after stopping heating.

Then, 20 g of flaxseed oil was added to the suspension, and the mixture was stirred uniformly in a manner of magnetic stirring or mechanical stirring, with a stirring speed being 800 rpm and a stirring time being 40 min. After that, high-speed shearing was performed on the above liquid at 10000 rpm for 3 min, and the high-speed shearing occurred every 30 s for 30 s. Finally, an ultrasonic cell disruptor was used at a power of 300 W for 10 min, and the ultrasonic homogenization was performed every 5 s for 5 s.

A peristaltic pump was used to transfer the prepared emulsion to a spray dryer SD-1500 for spray-drying. Spray-drying conditions were as follows: the inlet temperature was 180±5° C., the outlet air temperature was 70±5° C., the feed flow rate was 0.4 L/h, and the fan flow rate was 40 L/min. After spray-drying, highly unsaturated powdered oil with the flaxseed oil as a core material was prepared.

Example 7 Preparation of Highly Unsaturated Powdered Oil with Peony Seed Oil as Core Material 0.6 g of the hemp seed protein Pickering particles prepared in Example 1 were fully dissolved in 14 g of deionized water together with 2.7 g of maltodextrin and 2.7 g of corn syrup to prepare a hemp seed protein Pickering particle suspension. The dissolution conditions were as follows: initial stirring was firstly performed by using a glass rod or in a manner of mechanical stirring, magnetic stirring was then carried out for 30 min at 75° C. under the condition of a rotating speed being 700 rpm, and the product was stirred at room temperature for 12 h after stopping heating.

Then, 18 g of peony seed oil was added to the suspension, and the mixture was stirred uniformly in a manner of magnetic stirring or mechanical stirring, with a stirring speed being 800 rpm and a stirring time being 40 min. After that, high-speed shearing was performed on the above liquid at 10000 rpm for 3 min, and the high-speed shearing occurred every 30 s for 30 s. Finally, an ultrasonic cell disruptor was used at a power of 300 W for 10 min, and the ultrasonic homogenization was performed every 5 s for 5 s.

A peristaltic pump was used to transfer the prepared emulsion to a spray dryer SD-1500 for spray-drying. Spray-drying conditions were as follows: the inlet temperature was 175±5° C., the outlet air temperature was 70±5° C., the feed flow rate was 0.5 L/h, and the fan flow rate was 40 L/min. After spray-drying, highly unsaturated powdered oil with peony seed oil as a core material was prepared.

Comparative Example 1: Use of Conventional OSA-Starch Stabilized Emulsion 0.6 g of OSA-cassava starch was fully dissolved in 14 g of deionized water together with 2.7 g of maltodextrin and 2.7 g of corn syrup to prepare an OSA-cassava starch suspension. The dissolution conditions were as follows: initial stirring was firstly performed by using a glass rod or in a manner of mechanical stirring, magnetic stirring was then carried out for 30 min at 75° C. under the condition of a rotating speed being 700 rpm, and the product was stirred at room temperature for 12 h after stopping heating.

Then, 20 g of high oleic peanut oil, sunflower seed oil, safflower seed oil and flaxseed oil were added to the same amount of the above suspension respectively, and the mixture was stirred uniformly in a manner of magnetic stirring or mechanical stirring, with a stirring speed being 800 rpm and a stirring time being 40 min. After that, high-speed shearing was performed on the above liquid at 10000 rpm for 3 min, and the high-speed shearing occurred every 30 s for 30 s. Finally, an ultrasonic cell disruptor was used at a power of 300 W for 10 min, and the ultrasonic homogenization was performed every 5 s for 5 s.

Figure 7:
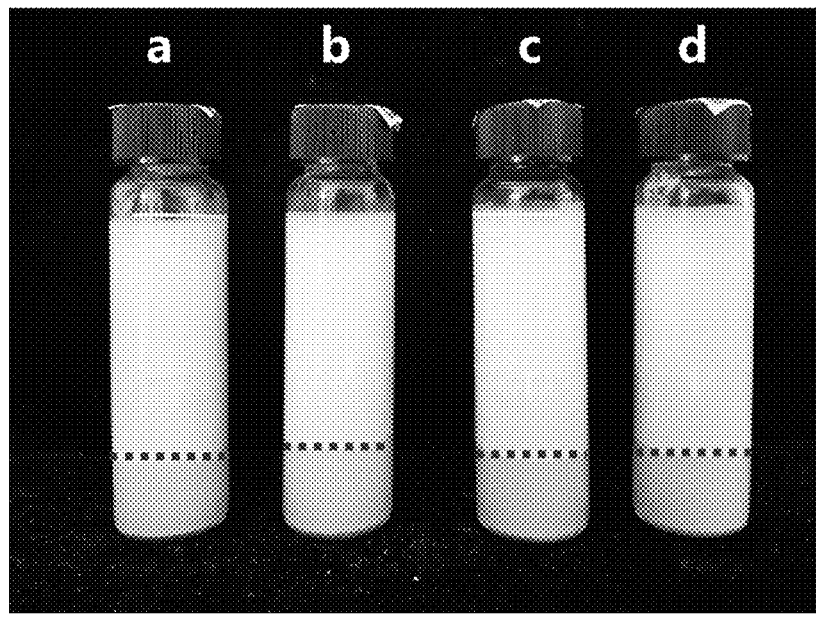
FIG. 7 shows Pickering emulsion stabilized with OSA-cassava starch (a. using high oleic peanut oil as a core material; b. using sunflower seed oil as a core material; c. using safflower seed oil as a core material; and d. using flaxseed oil as a core material).

The prepared emulsion was placed at room temperature for 24 h to observe the stability of the emulsion. The results are shown in FIG. 7. The emulsion stabilized with the OSA-cassava starch appeared stratification after being placed for 24 h, and thus its physical stability was poor.

Comparative Example 2: Study on the Stability of Pickering Emulsions Stabilized with Different Proteins Preparation of soybean residue Pickering particles: wet ball milling was used to treat dried soybean residue. The dried soybean residue was prepared into a 1.0 wt % suspension, stirred evenly, and then loaded into a ball milling tank. An agate grinding ball with a diameter of 2 mm was selected to rotate horizontally at a constant rate of 300 rpm for 10 h to obtain a loose powder sample.

Preparation of peanut protein Pickering particles: peanut protein isolate was prepared into a solution with a concentration of 15% (w/w), and the prepared solution was fully stirred, and then placed in a refrigerator at 4° C. for overnight refrigeration, so that the protein was fully hydrated. After 12 h, the protein solution was taken out, with a pH value adjusted to 7.0, and was heated in a water bath at 80° C. for 20 min. Then, TG enzyme was added, and cross-linking was carried out in a water bath at 45° C. for 4 h. The cross-linked protein was diluted and subjected to high pressure homogenization, so that colloidal particles were obtained.

Emulsions were prepared respectively by adopting the soybean residue Pickering particles, the peanut protein Pickering particles and hemp seed protein Pickering particles: the concentrations of the Pickering particles were diluted or adjusted to 3%, and flaxseed oil with a volume fraction of 50% was then added. After that, the mixture was stirred uniformly in a manner of magnetic stirring or mechanical stirring, with a stirring speed being 800 rpm and a stirring time being 40 min. Then, high-speed shearing was performed on the above liquid at 10000 rpm for 3 min, and the high-speed shearing occurred every 30 s for 30 s. Finally, an ultrasonic cell disruptor was used at a power of 300 W for 10 min, and the ultrasonic homogenization was performed every 5 s for 5 s.

After the emulsions were stored for 24 h, particle size analysis was performed by using a laser particle size analyzer S3500 from Microtrac Company, USA. The results are shown in Table 3.

TABLE 3

| Study on the stability of Pickering emulsions constructed with different proteins | | | |
|---|---|---|---|
| Serial number | Name of Pickering particles | 24 h particle size (nm) | 7 d particle size (nm) |
| 1 | Soybean residue | 1023 ± 205 | 2373 ± 16 |
| 2 | Peanut protein | 640 ± 88 | 771 ± 23 |
| 3 | Hemp seed protein | 419 ± 108 | 520 ± 7 |

Although the present disclosure has been disclosed as above in exemplary examples, it is not intended to limit the present disclosure. Anyone familiar with this technology can make various changes and modifications without departing from the technology and scope of the present disclosure. Therefore, the scope of protection of the present disclosure shall be as defined in the Claims.

What is claimed is:

1. A method for preparing hemp seed protein-containing Pickering emulsion, comprising:
    (1) crushing hemp seeds, removing oil from the hemp seeds by n-hexane solvent extraction and collecting a remaining solid part, and then performing alkali-soluble acid precipitation treatment on the remaining solid part to obtain a hemp seed protein powder;
    (2) dissolving the hemp seed protein powder in a formic acid solution to prepare a hemp seed protein stock solution, and then adding the hemp seed protein stock solution dropwise into deionized water under stirring conditions to form a suspension;
    (3) centrifuging the suspension, removing a bottom precipitate and then adjusting pH value, precipitating hemp seed protein nanoparticles, and then carrying out suction filtration to obtain a protein particle precipitate; and freeze-drying the protein particle precipitate to obtain dried hemp seed protein Pickering particles; and
    (4) adding the hemp seed protein Pickering particles, maltodextrin, and corn syrup solids into water for fully dissolving to form a homogeneous suspension, adding vegetable oil into the suspension prepared, and then mixing well to obtain Pickering emulsion;
    wherein the n-hexane has a ratio to the hemp seeds crushed of (5:1)-(10:1) (w/w).

2. The method of claim 1, wherein the alkali-soluble acid precipitation in (1) is performed at an alkali dissolution pH value of 8.0-11.0, and the acid precipitation pH value is 3.0-5.5.

3. The method of claim 1, wherein the formic acid solution has a ratio to the hemp seed protein powder of (10:1)-(20:1) (w/w).

4. The method of claim 1, wherein the protein stock solution has a ratio to the deionized water of (1:10)-(1:20) (v/v).

5. The method of claim 1, wherein the pH value is adjusted to 3.0-5.5 in (3).

6. A hemp seed protein-containing Pickering emulsion prepared by the method of claim 1.

* * * * *